Figure 1:
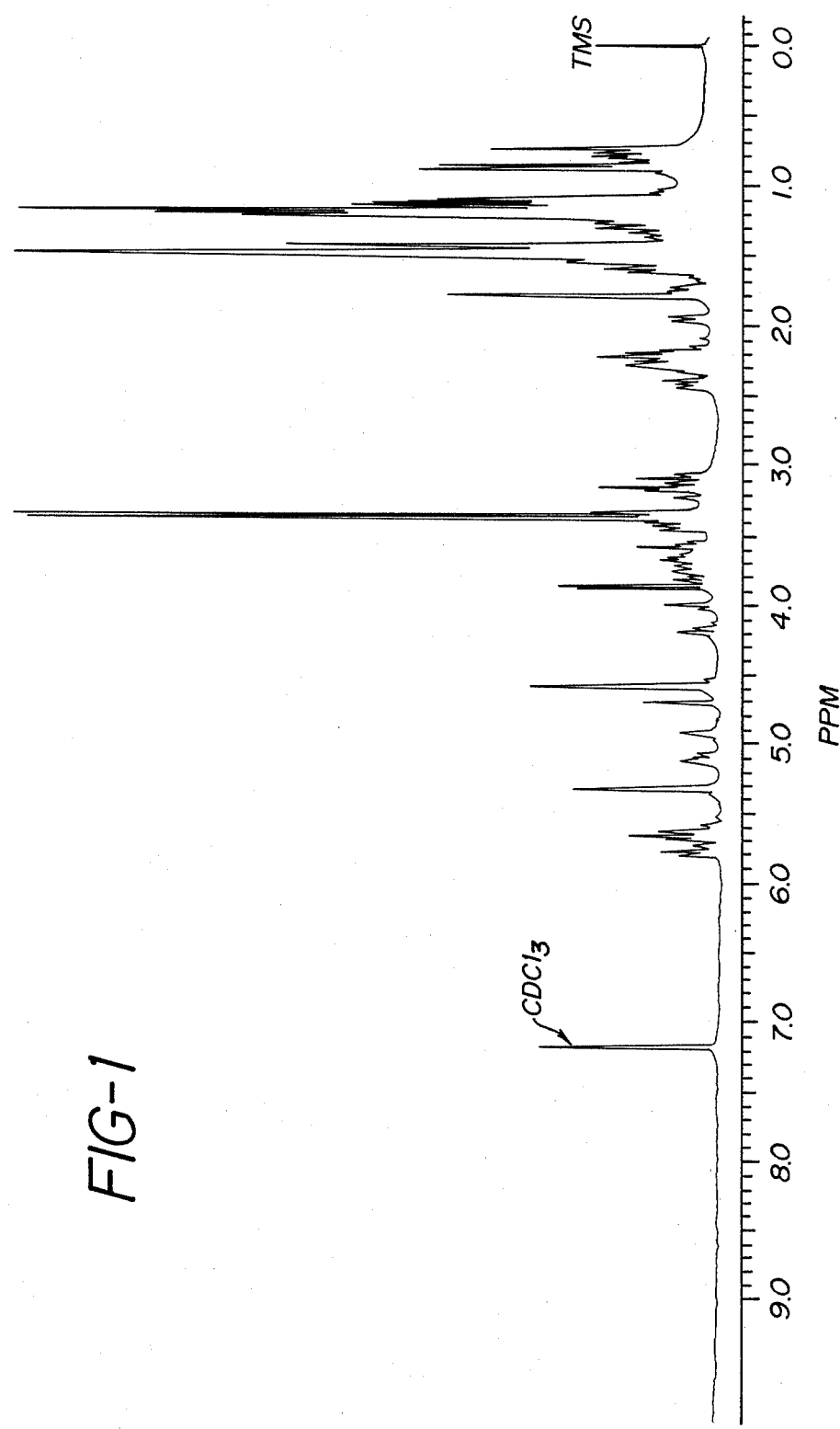

United States Patent [19]

Goegelman et al.

[11] Patent Number: 4,766,112
[45] Date of Patent: Aug. 23, 1988

[54] ANTHELMINTIC FERMENTATION PRODUCTS OF A MICROORGANISM

[75] Inventors: Robert T. Goegelman, Linden; Edward S. Inamine, Rahway; Raymond F. White, Englishtown, all of N.J.

[73] Assignee: Merck & Co. Inc., Rahway, N.J.

[21] Appl. No.: 857,670

[22] Filed: Apr. 30, 1986

Related U.S. Application Data

[63] Continuation-in-part of Ser. No. 759,780, Jul. 29, 1985, abandoned.

[51] Int. Cl.$^4$ ...................... A61K 31/71; C07H 17/08
[52] U.S. Cl. ...................................... 514/30; 536/7.1; 435/76; 435/119
[58] Field of Search ........................... 514/30; 536/7.1

[56] References Cited

U.S. PATENT DOCUMENTS 4,310,519  1/1982  Albers-Schonberg et al. ..... 536/7.1
4,378,353  3/1983  Goegelman et al. ................ 514/30

Primary Examiner—Ronald W. Griffin
Assistant Examiner—Elli Peselev
Attorney, Agent, or Firm—David L. Rose; Michael C. Sudol

[57] ABSTRACT

There are disclosed macrolides isolated from the fermentation broth, with avermectin Bla, avermectin Blb or 22,23-dihydro avermectin Bla as a substrate, of a known microorganism identified as MA-6181. The structure of the novel compounds isolated from the microorganism are presented based upon analytical studies. The compounds are highly potent antiparasitic, insecticidal, and anthelmintic agents. Compositions for such uses are also disclosed.

3 Claims, 3 Drawing Sheets

ANTHELMINTIC FERMENTATION PRODUCTS OF A MICROORGANISM

CROSS REFERENCE TO RELATED APPLICATIONS

This application is a continuation-in-part of our copending application Ser. No. 759,780 filed July 29, 1985 now abandoned.

BACKGROUND OF THE INVENTION

The instant novel compounds are related to the avermectin compounds disclosed in U.S. Pat. No. 4,310,519 and dihydro avermectin compounds disclosed in U.S. Pat. No. 4,199,569. However the instant compounds possess significant structural differences which readily differentiate them from the prior art compounds.

SUMMARY OF THE INVENTION

This invention is concerned with novel chemical compounds. In particular, it is concerned with novel macrocyclic lactones which are produced by the fermentation, with avermectin B1a, avermectin B1b or 22,23-dihydro avermectin B1a as substrates, of a nutrient medium with a strain of the microorganism *Nocardia autotrophica* MA-6181 which is a known microorganism available from the American Type Culture Collection as ATCC 35203. Thus, it is an object of this invention to provide for such novel compounds, and a method for preparing such products microbiologically. It is a further object of this invention to provide for the recovery and purification of such compounds from the fermentation broth. These substances have antiparasitic and insecticidal activity, in particular anthelmintic, acaricidal and nematocidal activity, and it is, thus, an additional object of this invention to provide novel anti-parasitic and insecticidal compositions containing the disclosed compounds. Further objects of this invention will become apparent from the following description of this invention.

DESCRIPTION OF THE INVENTION

In accordance with this invention, a novel substance is described, which is prepared by growing under controlled conditions, with, as a substrate avermectin B1a, avermectin B1b or 22,23-dihydro avermectin B1a, a known strain of microorganism, *Nocardia autotrophica* sub. sp. canberrica MA-6181. The compounds are obtained by fermentation and recovered in substantially pure form as described herein.

The culture designated MA-6181 is in the culture collection of Merck & Co., Inc., Rahway, N.J. A sample of this culture, capable of producing the herein described compound, is available in the permanent culture collection of the American Type Culture Collection at 12301 Parklawn Drive, Rockville, Md. 20852, and has been assigned the accession number ATCC 35203.

The instant compounds are produced from avermectin B1a, avermectin B1b or 22,23-dihydro avermectin B1a during the aerobic fermentation of suitable aqueous nutrient media under conditions described hereinafter, with a strain of *Nocardia autotrophica* MA-6181. Aqueous media such as those used for the production of many antibiotic substances are suitable for use in this process for the production of these macrocyclic compounds. Such nutrient media contain sources of carbon and nitrogen assimilable by the microorganism and generally low levels of inorganic salts. In addition, the fermentation media may contain traces of metals necessary for the growth of the microorganisms, and production of the desired compounds. These are usually present in sufficient concentrations in the complex sources of carbon and nitrogen, which may be used as nutrient sources, but can, of course, be added separately to the medium if desired.

In general, carbohydrates such as sugars, for example dextrose, sucrose, maltose, lactose, dextran, cerelose, corn meal, oat flour, and the like, and starches are suitable sources of assimilable carbon in the nutrient media. The exact quantity of the carbon source which is utilized in the medium will depend, in part, upon the other ingredients in the medium, but it is usually found that an amount of carbohydrate between 0.5 and 5% by weight of the medium is satisfactory. These carbon sources can be used individually or several such carbon sources may be combined in the same medium.

Various nitrogen sources such as yeast hydrolysates, yeast autolysates, yeast cells, tomato paste, corn meal, oat flour, soybean meal, casein hydrolysates, yeast extracts, corn steep liquors, distillers solubles, cottonseed meal, meat extract and the like, are readily assimilable by *Nocardia autotrophica* MA-6181 in the production of the instant compounds. The various sources of nitrogen can be used alone or in combination in amounts ranging from 0.2 to 6% by weight of the medium.

Among the nutrient inorganic salts, which can be incorporated in the culture media are the customary salts capable of yielding sodium, potassium, magnesium, ammonium, calcium, phosphate, sulfate, chloride, carbonate, and like ions. Also included are trace metals such as cobalt, manganese, and the like.

It should be noted that the media described hereinbelow and in the Examples are merely illustrative of the wide variety of media, which may be employed, and not intended to be limitative.

The following are Examples of media suitable for growing strains of *Nocardia autotrophica* MA-6181.

Medium 1

| | | |
|---|---|---|
| Dextrose | | 1.0 g |
| Dextrin (Fisher) | | 10.0 g |
| Beef Extract (Difco) | | 3.0 g |
| Yeast Autolysate (Ardamine pH, Yeast Prod.) | | 5.0 g |
| NZ Amine Type E (Sheffield) | | 5.0 g |
| $MgSO_4.7H_2O$ | | 0.05 g |
| Phosphate Buffer | | 2 ml |
| $CaCO_3$ | | 0.5 g |
| $dH_2O$ | | 1000 ml |
| | pH 7.0–7.2 | |
| Phosphate Buffer: | $KH_2PO_4$ | 91.0 g |
| | $Na_2HPO_4$ | 95.0 g |
| | $dH_2O$ | 1000 ml |
| | pH 7.0 | |

Medium 2

| | |
|---|---|
| Yeast Extract (Difco) | 4.0 g |
| Malt Extract (Difco) | 10.0 g |
| Dextrose | 4.0 g |
| $dH_2O$ | 1000 ml |
| Agar | 20 g |
| pH 7.2 | |

Medium 3

| Basal | |
|---|---|
| Sucrose | 103 g |
| K$_2$SO$_4$ | 0.25 g |
| Glucose | 10 g |
| L-Asparagine | 1.8 g |
| Casamino Acids (Difco) | 0.1 g |
| MgCl$_2$.6H$_2$O | 10.12 g |
| Trace Element Mix A | 2 ml |
| dH$_2$O | to 700 ml |
| Agar | 22.0 g |

Post-sterilization additions, per 700 ml Basal:

100 ml of CaCl$_2$ solution (29.5 g/1000 ml dH$_2$O)
100 ml of KH$_2$PO$_4$ solution (0.5 g/1000 ml dH$_2$O)
100 ml of Tes solution (0.3 g Tris HCl + 0.1 g EDTA + 0.14 g NaCl in 1000 ml dH$_2$O, adjust to pH 8.0)

Trace Element Mix A Composition:

| | |
|---|---|
| Fe(SO$_4$)$_3$.7H$_2$O | 250 mg |
| MnCl$_2$.4H$_2$O | 500 mg |
| CuCl$_2$.2H$_2$O | 25 mg |
| CaCl$_2$.2H$_2$O | 1000 mg |
| H$_3$BO$_3$ | 50 mg |
| (NH$_4$)$_6$Mo$_7$O$_{24}$.4H$_2$O | 20 mg |
| ZnSO$_4$.7H$_2$O | 100 mg |
| Co(NO$_3$)$_2$.6H$_2$O | 20 mg |
| 0.1 N HCl | 1000 ml |

Medium 4

| | |
|---|---|
| Dextrin (Fisher) | 40 g |
| Distillers Solubles (Grain Processing Corp.) | 7 g |
| Yeast Extract (Oxoid) | 5 g |
| CoCl$_2$.6H$_2$O | 50 mg |
| dH$_2$O | 1000 ml |
| pH 7.3 | |

Medium 5

| | |
|---|---|
| Dextrose | 45 g |
| Peptonized Milk (Sheffield) | 24 g |
| Ardamine pH (Yeast Products, Inc.) | 2.5 g |
| Polyglycol 2000 (Dow) | 2.5 ml |
| d/H$_2$O | 1000 ml |
| pH 7.0 | |

Medium 6

| | |
|---|---|
| Dextrose | 2.0% |
| Yeast Extract (Difco) | 2.0 |
| Casamino Acids (Difco) | 2.0 |
| KNO$_3$ | 0.2 |
| MgSO$_4$.7H$_2$O | 0.05 |
| NaCl | 0.05 |
| FeSO$_4$.7H$_2$O | 0.0025 |
| CaCl$_2$.2H$_2$O | 0.002 |
| ZnSO$_4$.7H$_2$O | 0.001 |
| MnSO$_4$.H$_2$O | 0.0005 |
| d H$_2$O | 1000 ml |
| pH 7.0 with NaOH | |

Medium 7

| | |
|---|---|
| Dextrose | 0.1% |
| Soluble Starch (Fisher) | 1.0 |
| Beef Extract (Difco) | 0.3 |
| Yeast Autolysate (Ardamine pH Yeast Products) | 0.5 |
| NZ Amine Type E (Sheffield) | 0.5 |
| MgSO$_4$.7H$_2$O | 0.005 |
| KH$_2$PO$_4$ | 0.0182 |
| Na$_2$HPO$_4$ | 0.0190 |

-continued

| | |
|---|---|
| CaCO$_3$* | 0.05 |
| d H$_2$O | 1000 ml |
| pH 7.0–7.2 with NaOH | |

*Added after pH adjustment

The fermentation employing *Nocardia autotrophica* MA-6181 can be conducted at temperatures ranging from about 20° C. to about 40° C. For optimum results, it is most convenient to conduct these fermentations at a temperature in the range of from about 24° C. to about 30° C. Temperatures of about 27°–28° C. are most preferred. The pH of the nutrient medium suitable for producing the instant compounds can vary from about 5.0 to 8.5 with a preferred range of from about 6.0 to 7.5.

Small scale fermentations are conveniently carried out by placing suitable quantities of nutrient media in a flask employing known sterile techniques, inoculating the flask with either spores or vegetative cellular growth of *Nocardia autotrophica* MA-6181 loosely stoppering the flask with cotton and permitting the fermentation to proceed in a constant temperature room of about 28° C. on a rotary shaker at from 95 to 300 rpm for about 2 to 10 days. For larger scale work, it is preferable to conduct the fermentation in suitable tanks provided with an agitator and a means of aerating the fermentation medium. The nutrient medium is made up in the tank and after sterilization is inoculated with a source of vegetative cellular growth of *Nocardia autotrophica* MA-6181. The fermentation is allowed to continue for from 1 to 8 days while agitating and/or aerating the nutrient medium at a temperature in the range of from about 24° to 37° C. The degree of aeration is dependent upon several factors such as the size of the fermentor, agitation speed, and the like. Generally the larger scale fermentations are agitated at about 95 to 500 RPM and about 2 to 20 cubic feet per minute (CFM) of air.

The separation of the novel compounds from the whole fermentation broth and the recovery of said compounds is carried out by solvent extraction and application of chromatographic fractionations with various chromatographic techniques and solvent systems.

The instant compounds have slight solubility in water, but are soluble in organic solvents. This property may be conveniently employed to recover the compounds from the fermentation broth. Thus, in one recovery method, the whole fermentation broth is combined with approximately an equal volume of an organic solvent. While any organic solvent may be employed, it is preferable to use a water immiscible solvent such as ethyl acetate, methylene chloride, chloroform and the like. Generally several extractions are desirable to achieve maximum recovery. The solvent removes the instant compounds as well as other substances lacking the antiparasitic activity of the instant compounds. If the solvent is a water immiscible one, the layers are separated and the organic solvent is evaporated under reduced pressure. If the solvent is water miscible, it can be extracted with a water immiscible solvent to separate the entrained water. This solvent can then be concentrated under reduced pressure. The residue is placed onto a chromatography column containing preferably, silica gel. The column retains the desired products and some impurities, but lets many of the impurities, particularly the nonpolar impurities, pass through. The column is washed with a moderately polar organic solvent such as methylene chloride or chloroform to further remove impurities, and is then washed with a mixture of methylene chloride or chloroform and an organic solvent of which acetone, ethyl acetate, methanol, and ethanol and the like are preferred. The solvent is evaporated and the residue further chromatographed using column chromatography, thin layer chromatography, preparative layer chromatography, high pressure liquid chromatography preferably reverse phase, and the like, with silica gel, aluminum oxide, dextran gels and the like, as the chromatographic medium, with various solvents and combinations of solvents as the eluent. Thin layer, high pressure, liquid and preparative layer chromatography may be employed to detect the presence of, and to isolate the instant compound. The use of the foregoing techniques as well as others known to those skilled in the art, will afford purified compositions containing the instant compound. The presence of the desired compound is determined by analyzing the various chromatographic fractions for biological activity against selected parasites, or physicochemical characteristics. The structure of the instant compounds has been determined by detailed analysis of the various spectral characteristics of the compounds, in particular their nuclear magnetic resonance, mass, ultraviolet and infrared spectra.

Figure 2:
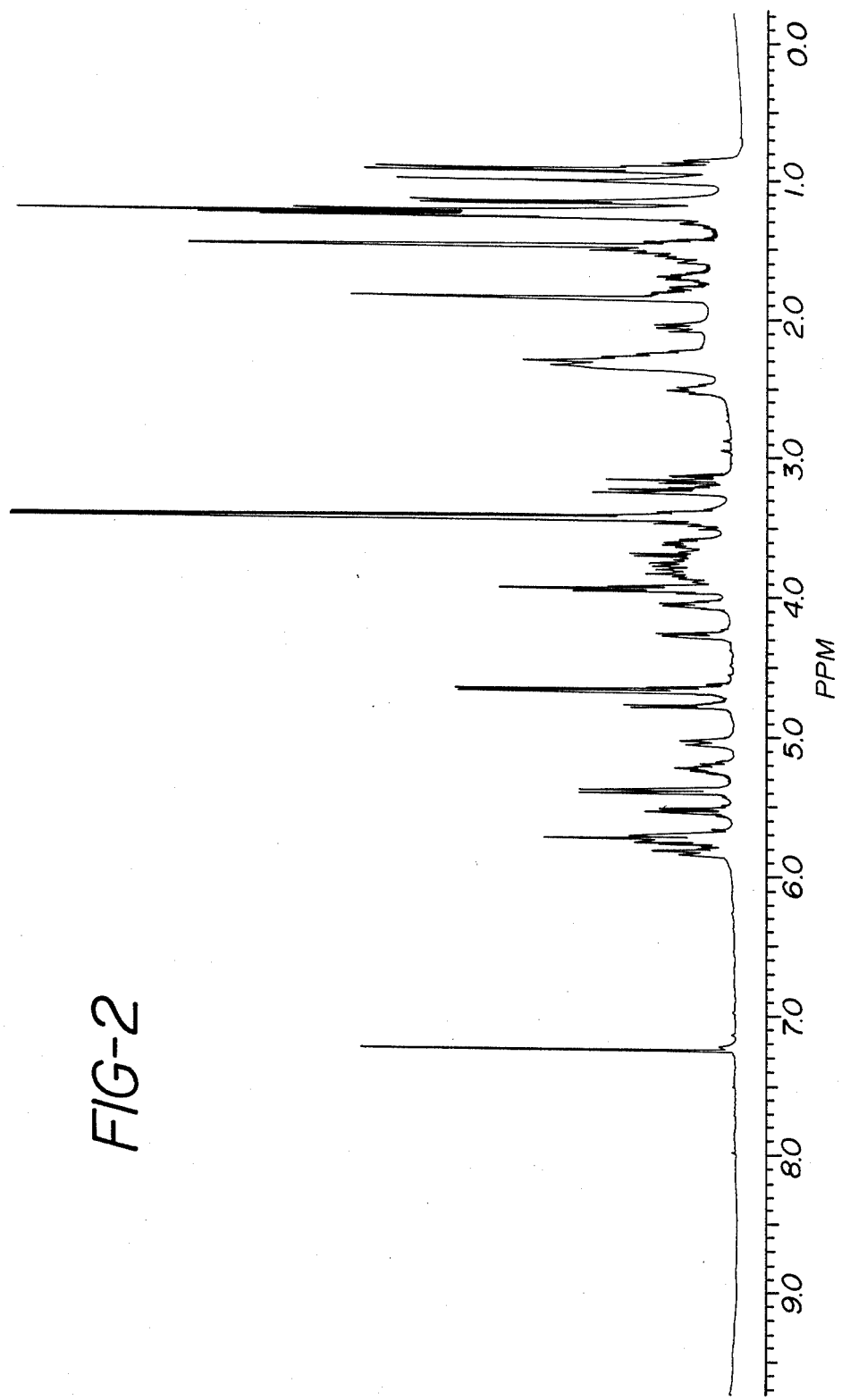
Figure 3:
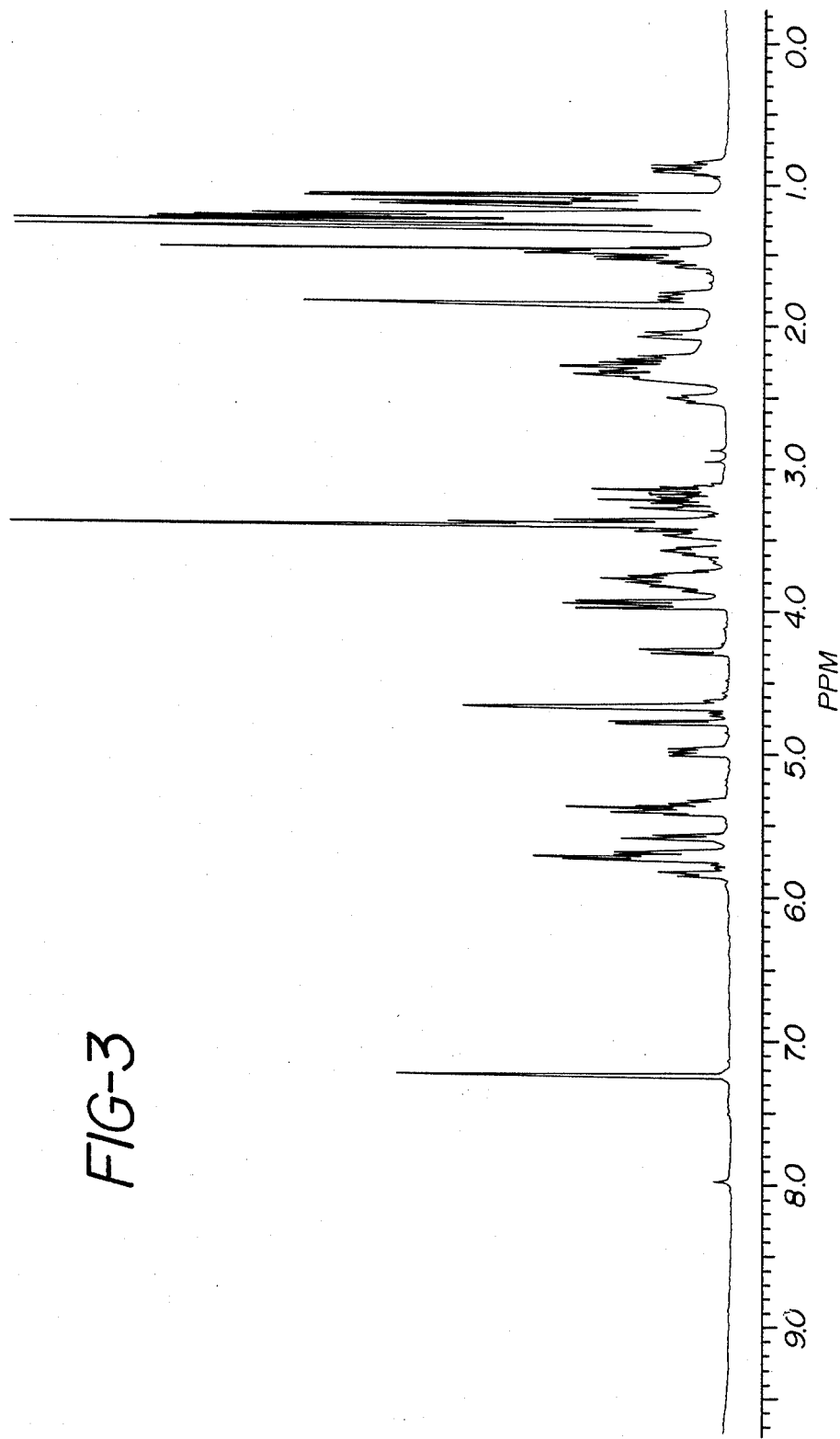

FIGS. 1, 2 and 3 attached hereto are the nuclear magnetic spectra of the compounds obtained in the instant invention identified below as compounds A, B and C respectively.

Based on these experimental data, the instant compounds are believed to have the following structural formula based upon the immediately preceding analytical data:

The compounds are assigned the names: (A) 27-hydroxy-22,23-dihydro avermectin B1a; (B) 27-hydroxy avermectin B1a; and (C) 26 hydroxy avermectin B1b.

| HR-MS | Found | Calculated | For | Assignment |
|---|---|---|---|---|
| A | 890.5023 | 890.5028 | $C_{48}H_{74}O_{15}$ | M+ |
| B | 870.4767 | 870.4766 | $C_{48}H_{70}O_{14}$ | M+ |
| C | 856.4606 | 856.4609 | $C_{47}H_{68}O_{14}$ | M+ |

The structure is as follows:

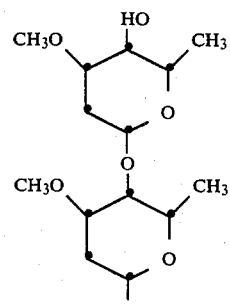

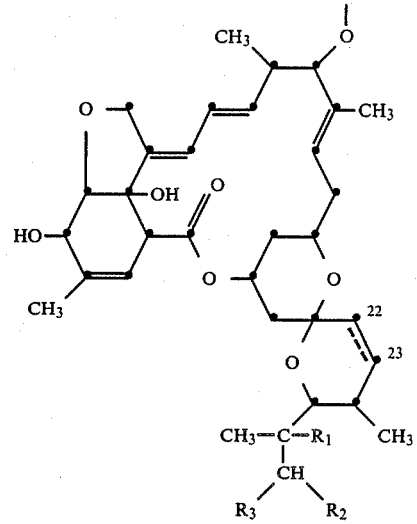

wherein $R_1$, $R_2$, $R_3$ and the broken line at the 22,23-positions have the following meanings:
 A—$R_1$=H, $R_2$=OH, $R_3$=$CH_3$, 22,23-single bond
 B—$R_1$=H, $R_2$=OH, $R_3$=$CH_3$, 22,23-double bond
 C—$R_1$=OH, $R_2$=H, $R_3$=H, 22,23-double bond.

The nuclear magnetic resonance spectrum for these compounds are found in the attached FIGS. 1-3 respectively and were originally recorded in $CDCl_3$ at ambient temperature on a Varian XL-400 NMR Spectrometer. Chemical shifts are shown in ppm relative to tetramethylsilane as an internal standard at zero ppm.

The novel compounds of this invention have significant parasiticidal activity as an anthelmintic, insecticide and acaricide, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia, and Oesophagostomum attack primarily the intestinal tract while others, such as Haemonchus and Ostertagia, are more prevalent in the stomach while other such as Dictyocaulus are found in the lungs. Still other parasites may be located in other tissues and organs of the body such as the heart and blood vessels, subcutaneous and lymphatic tissue and the like. The parasitic infections known as helminthiasis lead to anemia, malnutrition, weakness, weight loss, severe damage to the walls of the intestinal tract and other tissues and organs and, if left untreated, may result in death of the infected host. The compounds of this invention have unexpectedly high activity against these parasites, and in addition are also active against Dirofilaria in dogs, Nematospiroides, Syphacia, Aspiculuris in rodents, arthropod ectoparasites of animals and birds such as ticks, mites, lice, fleas, blowfly, in sheep Lucilia sp., biting insects and such migrating dipterous larvae as Hypoderma sp. in cattle, Gastrophilus in horses, and Cuterebra sp. in rodents.

The instant compounds are also useful against parasites which infect humans. The most common genera of parasites of the gastro-intestinal tract of parasites of man are Ancylostoma, Necator, Ascaris, Strongyloides, Trichinella, Capillaria, Trichuris, and Enterobius. Other medically important genera of parasites which are found in th blood or other tissues and organs outside the gastro-intestinal tract are the filiarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp. and the housefly *Musca domestica.*

The compounds are also useful against insect pests of stored grains such as Tribolium sp., Tenebrio sp. and of agricultural plants such as spider mites, (Tetranychus sp.), aphids (Acyrthiosiphon migratory orthopterans such as locusts and immature stages of insects living on plant tissue. The compounds are useful as a nematocide for the control of soil nematodes and plant parasites such as *Meloidogyne* spp. which may be of importance in agriculture.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or dicalcium phosphate.

Where it is desired to administer the instant compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compounds are to be administered via an animal feedstuff, they are intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparations using solketal, glycerol, formal and aqueous parenteral formulations are also used. The active compounds are dissolved or suspended in the parenteral formulation for administration; such formulations generally contain from 0.005 to 5% by weight of the active compound.

Although the antiparasitic agents of this invention finds its primary use in the treatment and/or prevention of helminthiasis, it is also useful in the prevention and treatment of diseases caused by other parasites, for example, arthropod parasites such as ticks, lice, fleas, mites and other biting insects in domesticated animals and poultry. They are also effective in treatment of parasitic diseases that occur in other animals including humans. The optimum amount to be employed for best results will, of course, depend upon the species of animal to be treated and the type and severity of parasitic infection or infestation. Generally, good results are obtained with our novel compounds by the oral administration of from about 0.001 to 10 mg per kg of animal body weight, such total dose being given at one time or in divided doses over a relatively short period of time such as 1–5 days. With the preferred compounds of the invention, excellent control of such parasites is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein is administered as a component of the feed of the animals, or dissolved or suspended in the drinking water, compositions are provided in which the active compound is intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active compound is intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned, the compounds of this invention are usually fed at concentrations of between 0.00001 to 0.002% in the feed in order to achieve the desired anti-parasitic result.

In addition, where the instant compound is to be added to an animal's feed, it is possible to utilize the dried mycelial cake from the fermentation broth. The mycelia contain a preponderance of the activity and since the level of the activity of the mycelia can be determined, it can be added directly to the animal's feed.

The compounds of this invention have a broad spectrum of activity against many internal parasites at low dosage levels and in many different animals. At levels of about 2.5 mg per kg of animal body weight, concentrated mixtures of the instant compounds are fully active in sheep against *Haemonchus contortus, Ostertagia circumcincta, Trichostrongylus axei, Trichostrongylus colubriformis,* Cooperia spp., and *Oesophagostomum columbianum*. Similarly in cattle at dosages as low as 0.043 mg/kg the instant compounds are fully active against *Ostertagia ostertage, Trichostrongylus axei, Trichostrongylus colubriformis, Oesophagostomum radiatum* and *Dictyocaulus viviparus*. In addition, horses infected with bots (*Gastrophilus intestinalis* and *Gastrophilus haemorrhoidalis*), large and small strongylus and Oxyuris are successfully treated with 10 mg/kg (about 1% active compound by weight) of a mixed concentrate of the instant compounds, and dogs infected with the microfilarial stage of heartworm (*Dirofilaria immitis*) are successfully treated with a single oral dose at 10 mg/kg (about 1% active compound by weight) of a concentrate of the instant compound. In rodents, such as mice, infections of Syphacia, Nematospiroides and Aspiculuris are successfully treated by the oral administration of the instant compound or of the concentrate obtained from the extraction of the mycelia.

The compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The anthelmintic activity of the instant compounds may be determined by orally administering via the feed, a sample of the individual compound, a concentrated extract, and the like to a mouse which had been infected 3 days earlier with *Nematospiroides dubius*. At 11, 12 and 13 days afer the initiation of the medication, the feces of the mouse are examined for *N. dubius* eggs, and on the next day the mouse is sacrificed and the number of worms present in the proximal portion of the small intestine are determined. An active compound is observed when there is a significant reduction of egg and worm counts when compared to infected, unmedicated controls.

The following examples are being provided in order that the instant invention may be more fully understood. Such examples are not to be construed as being limitative of the invention.

EXAMPLE 1

Transformation Methodology

| Media: | g/l |
|---|---|
| Seed Medium A | |
| Dextrose | 4.0 g |
| Nutrient Broth | 4.0 g |
| Yeast Extract | 4.0 g |
| Malt Extract | 10.0 g |
| 1000 ml distilled $H_2O$ pH 7.3 | |
| Slant Medium B | |
| Medium A plus Agar | 20.0 g |
| Transformation Medium C | |
| Same as Medium A, plus substrate at | 0.25 g |

A lyophile tube was aseptically opened and grown in seed Medium A (20 ml in a 250 ml 3-baffle Erlenmyer flask) for 48 hours on a rotary shaker (220 rpm) at 27° C.

This seed was then used to inoculate slants (Medium B), transformation flasks (Medium C), and to prepare frozen vials for future studies.

The substrate was added post sterilization and prior to inoculation. Methanol was used to solubilize the substrate for filter sterilization and addition. The transformation flasks (40 ml Medium C in 250 ml 3-baffle Erlenmyer flask) were incubated for 7 days with agitation (220 rpm) at 27° C. Following incubation, the whole broths were extracted as follows:

Extraction Methodology a. 50 ml methylene chloride were added to 40 ml whole broth and mechanically agitated for 15 minutes. The emulsion was broken by centrifugation and methylene chloride separated. Step "a" was repeated 3 times.

b. The pooled methylene chloride extracts were taken to dryness under vacuum.

c. The dried methylene chloride fraction was solubilized with 25 ml (x3) ethanol/0.1M $K_2HPO_4$, pH 7.0 (40/60). Three extracts pooled.

d. The phosphate buffer:ethanol fraction was extracted with 25 ml cyclohexane (x3) to remove the residual substrate. The cyclohexane fractions were pooled and taken to dryness under vacuum. The residue was solubilized with a known volume of methanol, dried with anhydrous $Na_2SO_4$ and, where appropriate, total radioactivity determined by scintillation counting.

e. The phosphate buffer:ethanol fraction previously extracted with cyclohexane, was then extracted with 25 ml methylene chloride (x3) to separate the altered substrate. The methylene chloride fractions were pooled and taken to dryness under vacuum. The residue was solubilized with a known volumn of methanol, dried with anhydrous $Na_2SO_4$ and total, where appropriate, radioactivity determined by scintillation counting.

f. All organic fractions were submitted for HPLC analysis to determine and isolate non-substrate avermectins.

Specific Example A

Culture: *Nocardia autotrophica* MA6181 ATCC 35203
Substrate: 1 mg $^3$H-22,23, dihydro avermectin B1a
Sample: Methylene chloride Ext. (A) $1.1 \times 10^6$ CPM Total
Sample: Cyclohexane Ext. (B) $4.0 \times 10^6$ CPM Total

Specific Example B

Culture: *Nocardia autotrophica* MA6181 ATCC 35203
Substrate: 25 mg 22,23, dihydro avermectin Bla Twenty five flasks pooled and extracted for product isolation and identification.
Sample: Cyclohexane Ext. (C)
Sample: Methylene chloride Ext. (D)

EXAMPLE 2

The final methylene chloride extract residue, sample D from Example 1B was dissolved in 400 microliters of 85/15 v/v methanol/water, filtered and the filtrate subjected to preparative HPLC chromatography on a DuPont Zorbax ODS reverse phase $C_{18}$ column 0.94×25 cm, at room temperature, using a solvent system of 85/15 v/v methanol/water at a flow rate of 4 ml/minute. The effluent stream was monitored at 243 nm using an LDC Spectromonitor II with a one mm path length cell at a setting of 0.64 AUFS, and a Spectra-Physics SP4100 computing integrator. Eleven fractions were collected. Fraction ten, 22.5 minutes to 25.5 minutes, was concentrated to dryness. The residue was taken up in 1 ml of methanol and labeled Sample E.

EXAMPLE 3

The cyclohexane extract residue, sample C from Example 1B was dissolved in 700 mcl of 85/15 v/v methanol/water, filtered and the filtrate subjected to preparative HPLC chromatography on a DuPont Zorbax ODS reverse phase $C_{18}$ column 0.94×25 cm, at room temperature using a solvent system of 85/15 v/v methanol/water at a flow rate of 4 ml/minute. The effluent stream was monitored at 243 nm using an LDC Spectromonitor II with a one mm path length cell at a setting of 0.32 AUFS, and a Spectra-Physics SP4100 computing integrator. Eleven fractions were collected. Fraction three, 23 minutes to 25.5 minutes, was concentrated to dryness. The residue was taken up in one-half ml of methanol and labeled Sample F.

Samples E and F were combined in 5 ml of methanol and labeled G. Ultraviolet quantitation of solution carried out as follows: assaying at a dilution of 1:5 in methanol.

$$\text{Conc } X = \frac{O.D. \text{ 244 nm} \times 10 \times \text{dilution}}{0.365} \times \text{volume}$$

$$\text{Conc } X = \frac{2.190 \times 10 \times 5}{0.365} \times 5 = 1{,}500 \text{ mcg}$$

EXAMPLE 4

Sample G from Example 3 was concentrated to dryness and the residue taken up in 200 mcl of methanol and subjected to preparative HPLC chromatography on a DuPont Zorbax ODS $C_{18}$ reverse phase column 0.94×25 cm at room temperature using a solvent system of 85/15 v/v methanol/water at a flow rate of 4 ml/minute for thirty-four minutes followed by a gradient of 85% methanol to 100% methanol over five minutes at 4 ml/minute and maintaining at 100% methanol for seventy-six minutes.

The effluent system was monitored at 243 nm using an LDC Spectromonitor II with a one mm path length cell at a setting of 0.32 AUFS, and a SpectraPhysics SP4100 computing integrator. Seven fractions were collected. Fraction six, 27 minutes to 29 minutes was concentrated to dryness. The residue was taken up in 10 ml of methanol and diluted 1:5 with methanol for ultraviolet quantitation. Sample labeled H.

$$\text{Conc } X = \frac{O.D. \text{ 244 nm} \times 10 \times \text{dilution}}{0.365} \times \text{volume}$$

$$H = \frac{0.450 \times 10 \times 5}{0.365} \times 10 = 616 \text{ mcg}$$

Sample H assigned the structure 27-hydroxy-22,23-dihydro avermectin Bla. FIG. 1 is the nuclear magnetic resonance spectrum for this compound.

EXAMPLE 5

The transformation and extraction methodology of Example 1 was repeated for the following Specific Examples.

Specific Example C

Culture: *Nocardia autotrophica* MA-6181, ATCC-35203
Substrate: 2 mg Avermectin Bla
Sample: Methylene chloride Ext. (E)

Specific Example D

Culture: *N. autotrophica* MA-6181, ATCC-35203
Substrate: 1 mg Avermectin Bla
Sample: Methylene chloride Ext. (E)

Specific Example E

Culture: *N. autotrophica* MA-6181, ATCC-35203
Substrate: 45 mg Avermectin Bla Forty-five flasks pooled for product isolation and identification.
Sample: Methyl chloride Ext. (E)

Specific Example F

Culture: *N autotrophica* MA-6181, ATCC-35203
Substrate: 50 mg Avermectin Bla Fifty flasks pooled for product isolation and identification
Sample: Methylene chloride Ext. (E)

EXAMPLE 6

Sample E from Specific Example E was concentrated to 0.5 ml in methanol and filtered. The filter was washed with 0.1 ml of methanol and the filtrate and wash combined. The combined filtrate and wash was subjected to preparative HPLC chromatography on a DuPont Zorbax ODS C18 column 0.94×25 cm. maintained at room temperature. The chromatography was carried out using a solvent of 80/20 v/v methanol/water at a flow rate of 4 ml/minute. The effluent stream was monitored at 243 nm using an L.D.C. Spectro-Monitor-II with a 1 mm path length cell and a setting of 0.64 AUFS. Thirty-one fractions were collected based on the ultra-violet trace. Selected fractions were concentrated to dryness and taken up in 1 ml of methanol for quantitation. The samples were quantitated using an analytical HPLC system of 80/20 v/v methanol/water at 1 ml/minute and a DuPont Zorbax ODS C18 column 0.46×25 cm maintained at 27° C., monitoring the effluent at 243 nm. The sample concentrations were calculated as follows:

$$\text{Concentration of } X = \frac{\text{Total area counts of } X}{\text{area counts/mcg avermectin-Bla}}$$

Fractions 13 and 14 were found to contain 1.53 and 0.24 mg respectively of the desired compound. Fractions 13 and 14 were combined and labeled Sample E-1 which was identified as 27-hydroxy-avermectin-Bla. FIG. 2 is the nuclear magnetic resonance spectrum for this compound.

EXAMPLE 7

The transformation and extraction methodology of Example 1 was repeated for the following Specific Examples:

Specific Example G

Culture: *Nocardia autotrophica* MA-6181, ATCC-35203
Substrate: 2 mg Avermectin Blb
Sample: Methylene chloride Ext. (F)

Specific Example H

Culture: *N. autotrophica* MA-6181, ATCC-35203
Substrate: 1 mg Avermectin Blb
Sample: Methylene chloride Ext. (F)

Specific Example I

Culture: *N. autotrophica* MA-6181, ATCC-35203
Substrate: 45 mg Avermectin Blb Forty-five flasks pooled for product isolation and identification.
Sample: Methylene chloride Ext. (F)

EXAMPLE 8

Sample F from Specific Example I was concentrated to dryness and the residue taken up in 0.5 ml of methanol. This solution was filtered and the filtrate subjected to preparative HPLC chromatography on a DuPont Zorbax ODS C18 column 0.94×25 cm at room temperature. The chromatography was carried out at 4 ml/minute using the following gradient developed by an Du-Pont 8800 gradient controller.

Gradient: 75/25 methanol/water for 68 minutes than a linear gradient over one minute to 77/23 methanol/water, hold for 23 minutes, then a linear gradient over one minute to 79/21 methanol water, hold for 30 minutes then linear gradient to 100% methanol over 10 minutes, hold for 30 minutes.

The effluent stream was monitored at 243 nm using an L.D.C. Spectro-Monitor-II with a 1 mm path length cell and a setting of 1.28 AUFS. Thirty fractions were collected based on the ultra-violet trace. Selected fractions were concentrated to dryness and taken up in 1 ml of methanol for quantitation. The selected fractions were quantitated using an analytical HPLC system of 80/20 v/v methanol/water at 1 ml/minute and a Du-Pont Zorbax ODS C18 column 0.46×25 cm maintained at 27° C., monitoring the effluent at 243 nm. The sample concentrations were calculated as follows:

$$\text{Conc. } X = \frac{\text{area counts of } X}{\text{area counts/mcg avermectrin-Bla}} \times \frac{M.W. \ X}{M.W. \ \text{Bla}}$$

Fraction 10 contained 1.3 mg of 26-hydroxy-avermectin-Blb and fraction 23 contained 0.61 mg of 3″—O—desmethyl-avermectin-Blb. FIG. 3 is the nuclear magnetic resonance spectrum for 26-hydroxy-avermectin Blb.

What is claimed is:

1. A compound having the formula:

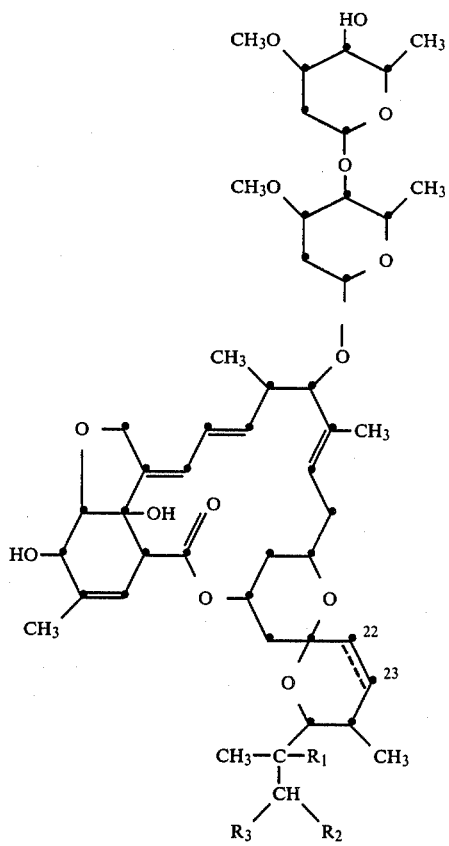

wherein $R_1$, $R_2$, n and the broken line at the 22,23-positions have the following meanings:

Compound A where $R_1$=H, $R_2$=OH, $R_3$=CH$_3$, 22,23-single bond

Compound B where $R_1$=H, $R_2$=OH, $R_3$=CH$_3$, 22,23-double bond

Compound C where $R_1$=OH, $R_2$=H, $R_3$=H, 22,23-double bond.

2. A method for the treatment of parasitic diseases in animals which comprises administering to an animal infected with parasites, an effective amount of a compound of claim 1.

3. A composition useful for the treatment of parasitic diseases which comprises an inert carrier and from 0.001 to 5% of a compound of claim 1.

* * * * *

UNITED STATES PATENT AND TRADEMARK OFFICE
CERTIFICATE OF CORRECTION

PATENT NO. : 4,766,112

DATED : August 23, 1988

INVENTOR(S) : Robert T. Goegelman, Edward S. Inamine & Raymond F. White

It is certified that error appears in the above-identified patent and that said Letters Patent is hereby corrected as shown below:

In column 5, lines 51 and 52, delete "$M^+$" from each line and insert therefore --$(M-H_2O)^+$--.

Signed and Sealed this

Twenty-sixth Day of September, 1989

Attest:

DONALD J. QUIGG

*Attesting Officer*  *Commissioner of Patents and Trademarks*